United States Patent
Mathur et al.

(10) Patent No.: US 9,545,282 B2
(45) Date of Patent: Jan. 17, 2017

(54) BONE GRAFT DELIVERY APPARATUS

(71) Applicant: EBI, LLC, Parsippany, NJ (US)

(72) Inventors: Surinder Saran Mathur, Irvine, CA (US); Steven Kenneth Lee, Anaheim, CA (US)

(73) Assignee: EBI, LLC, Parsippany, NJ (US)

( * ) Notice: Subject to any disclaimer, the term of this patent is extended or adjusted under 35 U.S.C. 154(b) by 958 days.

(21) Appl. No.: 13/791,925

(22) Filed: Mar. 9, 2013

(65) Prior Publication Data
US 2014/0257232 A1 Sep. 11, 2014

(51) Int. Cl.
*A61B 17/88* (2006.01)
*A61F 2/46* (2006.01)
(Continued)

(52) U.S. Cl.
CPC ......... *A61B 17/8825* (2013.01); *A61F 2/4601* (2013.01); *A61F 2/4611* (2013.01);
(Continued)

(58) Field of Classification Search
CPC .. A61B 17/8825; A61F 2/4601; A61F 2/4611; A61F 2002/30522; A61F 2002/30617; A61F 2002/4627; A61F 2310/00359; A61M 5/46; A61M 5/31593; A61M 31/007; A61M 37/0069
(Continued)

(56) References Cited

U.S. PATENT DOCUMENTS 3,486,505 A 12/1969 Morrison
3,520,299 A 7/1970 Lott et al.
(Continued)

FOREIGN PATENT DOCUMENTS

CN 1194575 A 9/1998
CN 101854886 A 10/2010
(Continued)

OTHER PUBLICATIONS

Extended European search report dated Jun. 5, 2014 from related application.
(Continued)

*Primary Examiner* — Todd E Manahan
*Assistant Examiner* — Marcela I Shirsat
(74) *Attorney, Agent, or Firm* — Schwegman Lundberg & Woessner, P.A.

(57) ABSTRACT

A magazine supporting multiple bone grafts in chambers is coupled to a housing including a barrel. A plunger selectively passes through one of the chambers and along the barrel. A trigger mechanism advances the plunger along the barrel. A selector knob is movable into a plurality of positions, wherein each position employs one of a plurality of stops. One stop prevents the end of plunger from advancing past a predetermined ready position short of the end of the barrel when selected. Another stop prevents the plunger from advancing past a predetermined dispensing position substantially aligned with the end of the barrel when selected. Another stop prevents the plunger from advancing past a predetermined manipulating position beyond the end of the barrel when selected. In the manipulating position, the distal end of the plunger can be used to reposition the bone graft within the spinal disc cavity. Related methods are also provided.

14 Claims, 6 Drawing Sheets

(51) Int. Cl.
  *A61M 5/315* (2006.01)
  *A61M 5/46* (2006.01)
  *A61F 2/30* (2006.01)

(52) U.S. Cl.
  CPC ............. *A61F 2002/30522* (2013.01); *A61F 2002/30617* (2013.01); *A61F 2002/4627* (2013.01); *A61F 2310/00359* (2013.01); *A61M 5/31593* (2013.01); *A61M 5/46* (2013.01)

(58) Field of Classification Search
  USPC ................................ 604/500, 191, 181, 187
  See application file for complete search history.

(56) References Cited

U.S. PATENT DOCUMENTS

| | | | |
|---|---|---|---|
| 3,774,607 | A | 11/1973 | Schmitz |
| 4,072,254 | A | 2/1978 | Cox |
| 4,081,111 | A | 3/1978 | Sandow |
| 4,531,938 | A | 7/1985 | Kaye et al. |
| 4,576,591 | A | 3/1986 | Kaye et al. |
| 4,673,387 | A | 6/1987 | Phillips et al. |
| 4,762,515 | A | 8/1988 | Grimm |
| 5,697,932 | A | 12/1997 | Smith et al. |
| 7,824,359 | B2 | 11/2010 | Solomon et al. |
| 8,118,813 | B2 | 2/2012 | Perez-Cruet et al. |
| 8,246,572 | B2 | 8/2012 | Cantor et al. |
| 8,333,729 | B2 | 12/2012 | Discher, Jr. et al. |
| 9,089,679 | B2 * | 7/2015 | Fontana ................ A61D 1/025 |
| 2002/0116006 | A1 | 8/2002 | Cohen |
| 2003/0236573 | A1 | 12/2003 | Evans |
| 2008/0319446 | A1 * | 12/2008 | Young ................ A61B 17/8822 606/93 |

FOREIGN PATENT DOCUMENTS

WO   WO 2009/137361   11/2009
WO   WO 2013014505 A1 *  1/2013 ............. A61D 1/025

OTHER PUBLICATIONS

Actifuse Shape Instructions for Use R2; Apatech LTD—25013; Oct. 8, 2009.
Altius M-Ini; Occipito-Cervice-Thoracic System; Surgical Technique; Biomet Spine; Biomet, Inc.; 2007.
Biomet Vertebroplasty System; Surgical Technique; Biomet Spine; Biomet, Inc.; 2007.
Indux Cancellous Sponge and Indux Cancellous Strip; Biomet, Inc.; 2013.
Cox Medical; Denpress; coxmedical.com website, original date unknown.
Cox North America; COX North America, Inc.; cox-applicators.com website, original date unknown.
"Chinese Application Serial No. 201410082901X, Office Action mailed Oct. 10, 2015", 9 pgs.

* cited by examiner

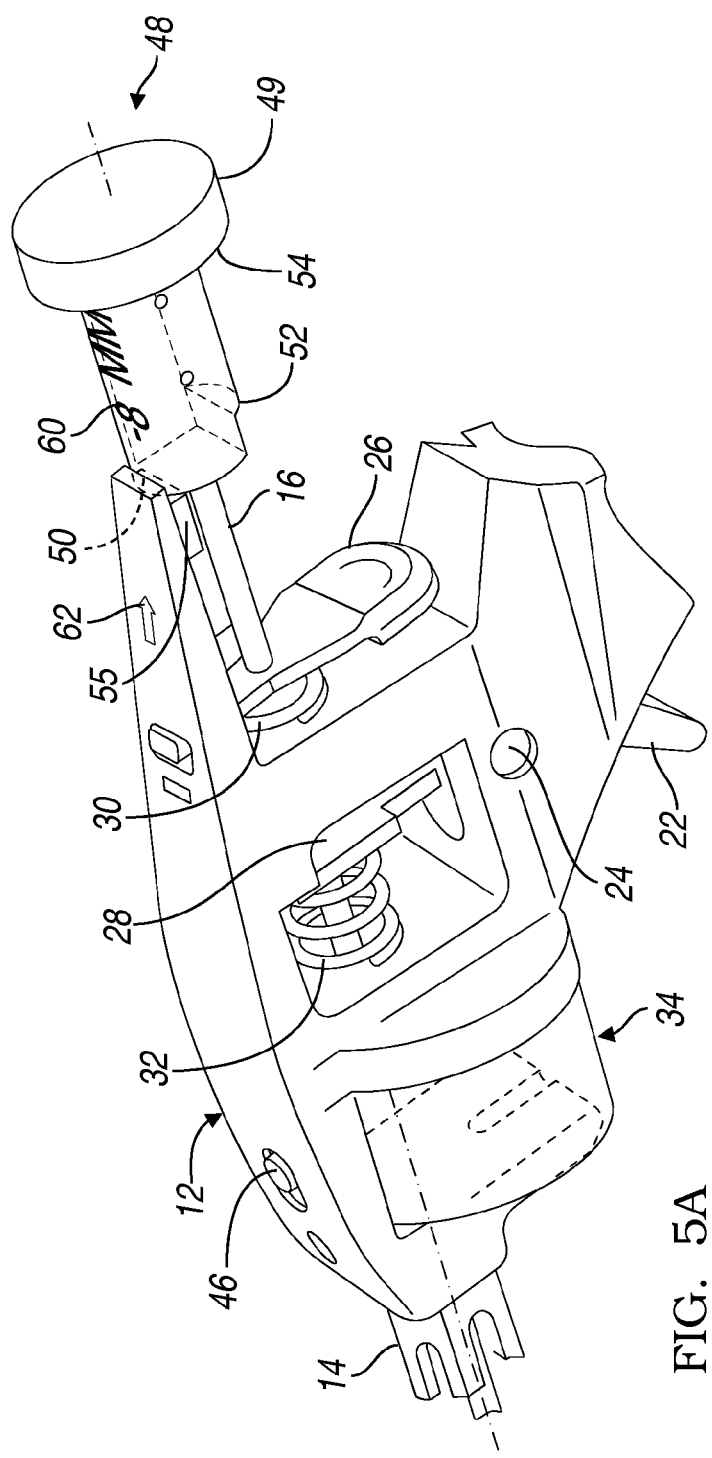
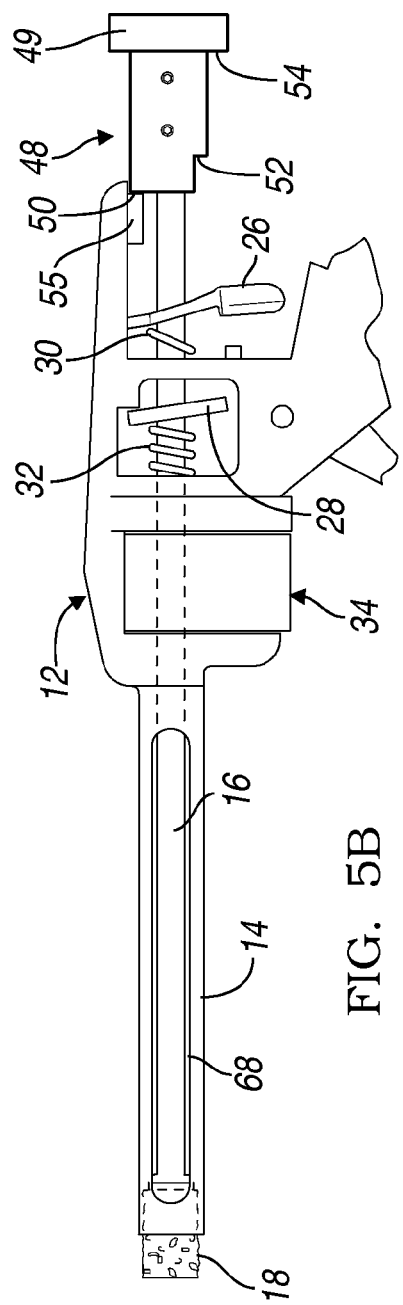
FIG. 5A
FIG. 5B

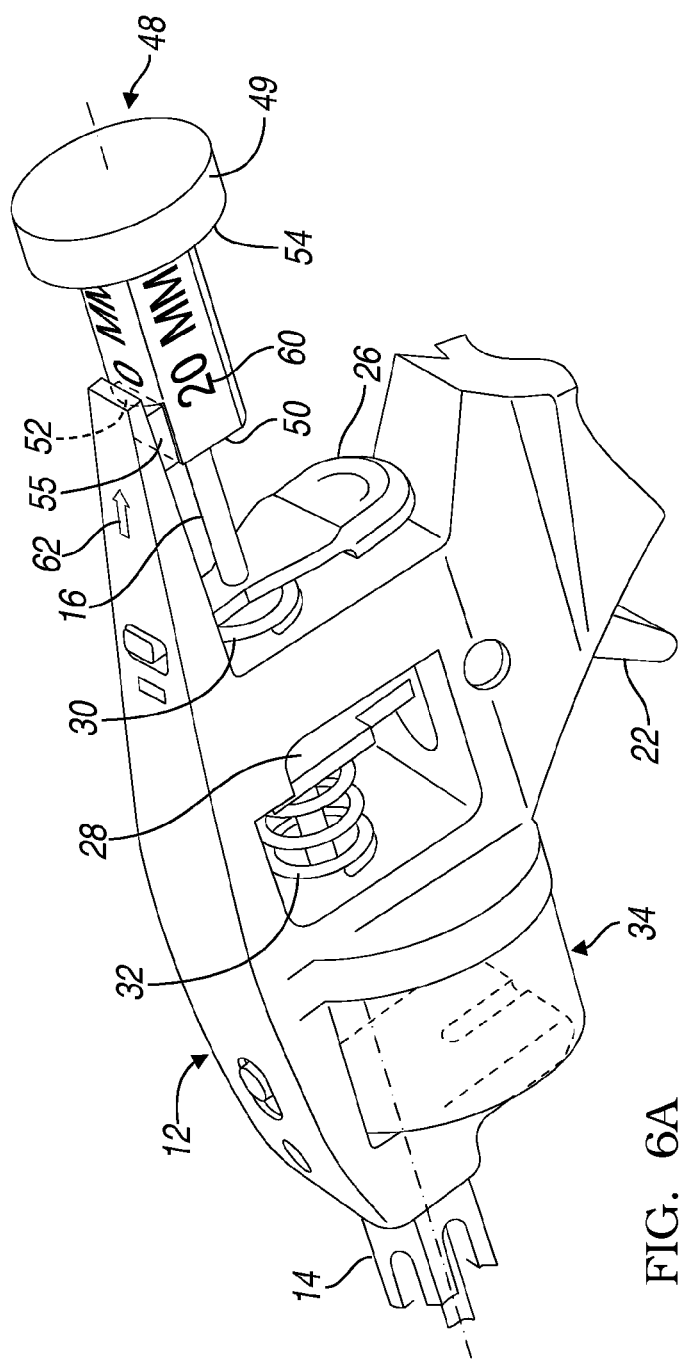
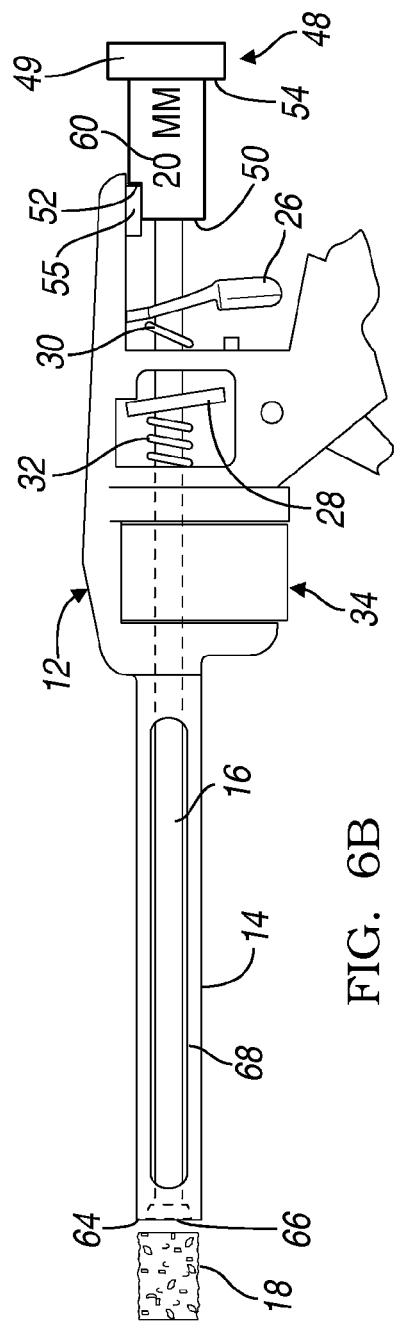
FIG. 6A
FIG. 6B

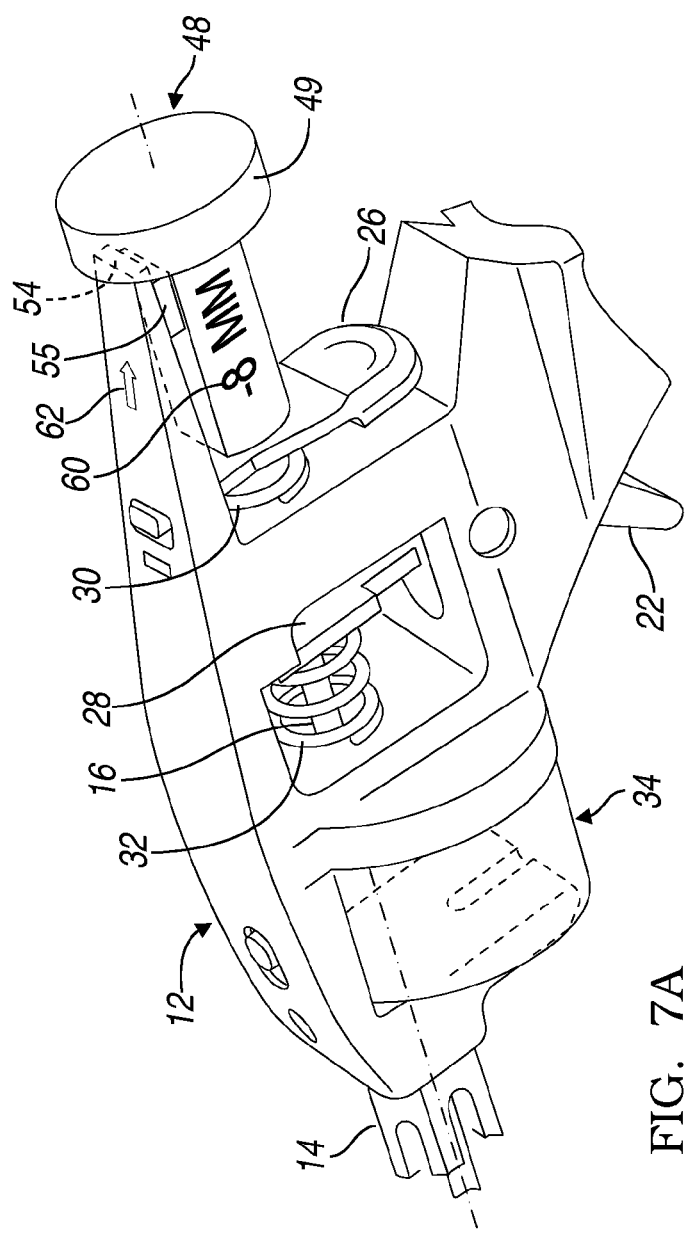
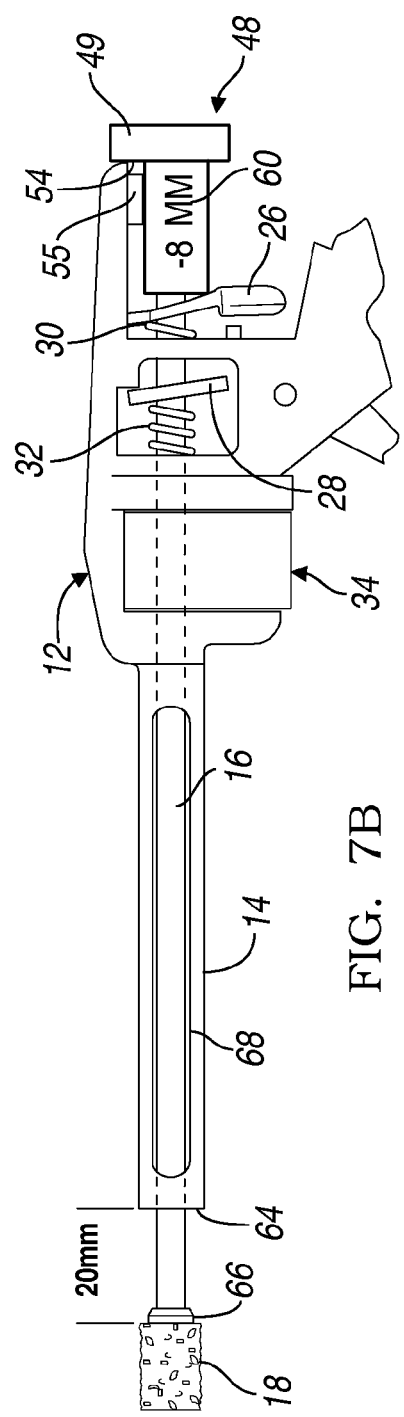
FIG. 7A
FIG. 7B

BONE GRAFT DELIVERY APPARATUS

FIELD

The present disclosure relates to a bone graft delivery apparatus.

BACKGROUND

This section provides background information related to the present disclosure which is not necessarily prior art.

The human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue or correct the deformity, which can require the use of one or more implants such as bone grafts.

In one example, in order to restore function to or correct a deformity of the spinal column, posterior lumbar interbody fusion (PLIF) surgery can be performed through the posterior part of the spine. This technique can also be used through other lumbar approaches, such as anterior, postero-lateral, as well as through various approaches in the thoracic and cervical spinal regions. During such surgery, hardware such as pedicle screws and rods can be attached to the back of the vertebra to stabilize the spine and to enhance the fusion rate. One or more intervertebral implants or spacers can also be used to further stabilize the spine. Bone grafts are inserted into the disc space from one side of the spine. Delivering and positioning the bone grafts into and within the disc space can be problematic.

SUMMARY

This section provides a general summary of the disclosure, and is not a comprehensive disclosure of its full scope or all of its features.

In accordance with one particular aspect, the present teachings provide a bone graft delivery apparatus. The apparatus includes a housing including a barrel and a handle. A magazine is coupled to the housing and has a plurality of chambers. Each of the chambers is configured to support a bone graft. A plunger is supported by the housing and is configured to selectively pass through one of the chambers and along the barrel. A selector knob is operably coupled to a plurality of stops that are coupled to the plunger. The selector knob is movable into a plurality of positions, wherein each position employs one of the stops. A trigger mechanism is supported by the housing and is operably coupled to the plunger to advance the plunger along the barrel. A first of the stops prevents the plunger from being moved forward past a first predetermined plunger position when the selector knob is in a first of the positions. A second of the stops prevents the plunger from being moved forward past a second predetermined plunger position when the selector knob is in a second of the positions.

In accordance with another particular aspect, the present teachings provide a bone graft delivery apparatus. The apparatus includes a housing including a barrel and a handle. A magazine is rotatably coupled to the housing and has a plurality of chambers. Each of the chambers is configured to support a bone graft. A plunger is supported by the housing and is configured to selectively pass through one of the chambers and along the barrel. A selector knob is operably coupled to a plurality of stops that are coupled to the plunger. The selector knob is movable into a plurality of positions, wherein each position employs one of the stops. A trigger mechanism is supported by the housing and is operably coupled to the plunger to advance the plunger along the barrel. A first of the stops prevents a distal end of the plunger from moving beyond a first predetermined plunger distal end position that is short of a distal end of the barrel when the selector knob is in a first of the positions. A second of the stops prevents the distal end of the plunger from moving beyond a second predetermined plunger distal end position that is beyond the distal end of the barrel when the selector knob is in a second of the positions.

In accordance with still yet another particular aspect, the present teachings include a method of providing a bone graft delivery apparatus. The method includes configuring a longitudinal passageway and a plunger movable along the passageway to push a bone graft along the passageway. A stop mechanism is configured to selectively prevent the plunger from moving past a predetermined ready position with the bone graft being held by the passageway adjacent a distal end of the passageway. The stop mechanism is also configured to selectively prevent the plunger from moving past a predetermined dispensing position with a distal end of the plunger substantially aligned with the distal end of the passageway. The stop mechanism is additionally configured to selectively permit the plunger to move past the predetermined dispensing position to extend the plunger beyond the distal end of the passageway.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5A is a partial perspective view of the apparatus of FIG. 1 illustrated the stop and selector member in a first stop position.

FIG. 5B is a partial side elevation view of the apparatus showing both the stop and selector member and the distal end of the plunger in the first stop position of FIG. 5A.

FIG. 6A is a partial perspective view of the apparatus of FIG. 1 illustrated the stop and selector member in a second stop position.

FIG. 6B is a partial side elevation view of the apparatus showing both the stop and selector member and the distal end of the plunger in the second stop position of FIG. 6A.

FIG. 7A is a partial perspective view of the apparatus of FIG. 1 illustrated the stop and selector member in a third stop position.

FIG. 7B is a partial side elevation view of the apparatus showing both the stop and selector member and the distal end of the plunger in the third stop position of FIG. 5A.

Corresponding reference numerals indicate corresponding parts throughout the several views of the drawings.

DETAILED DESCRIPTION

Example embodiments will now be described more fully with reference to the accompanying drawings.

Figure 1:
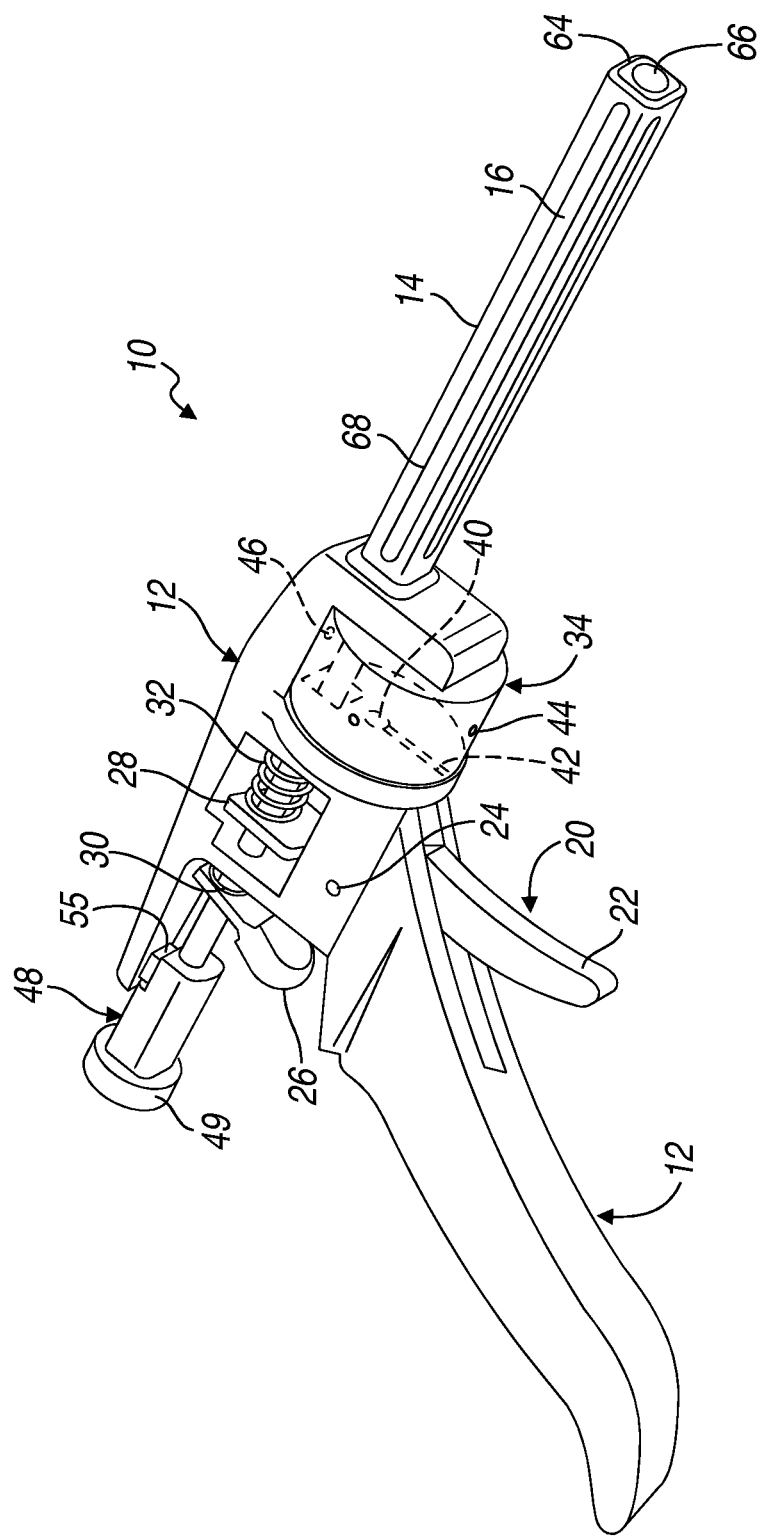
FIG. 1 is a perspective view of a bone graft delivery apparatus constructed in accordance with the present teachings.
Figure 2:
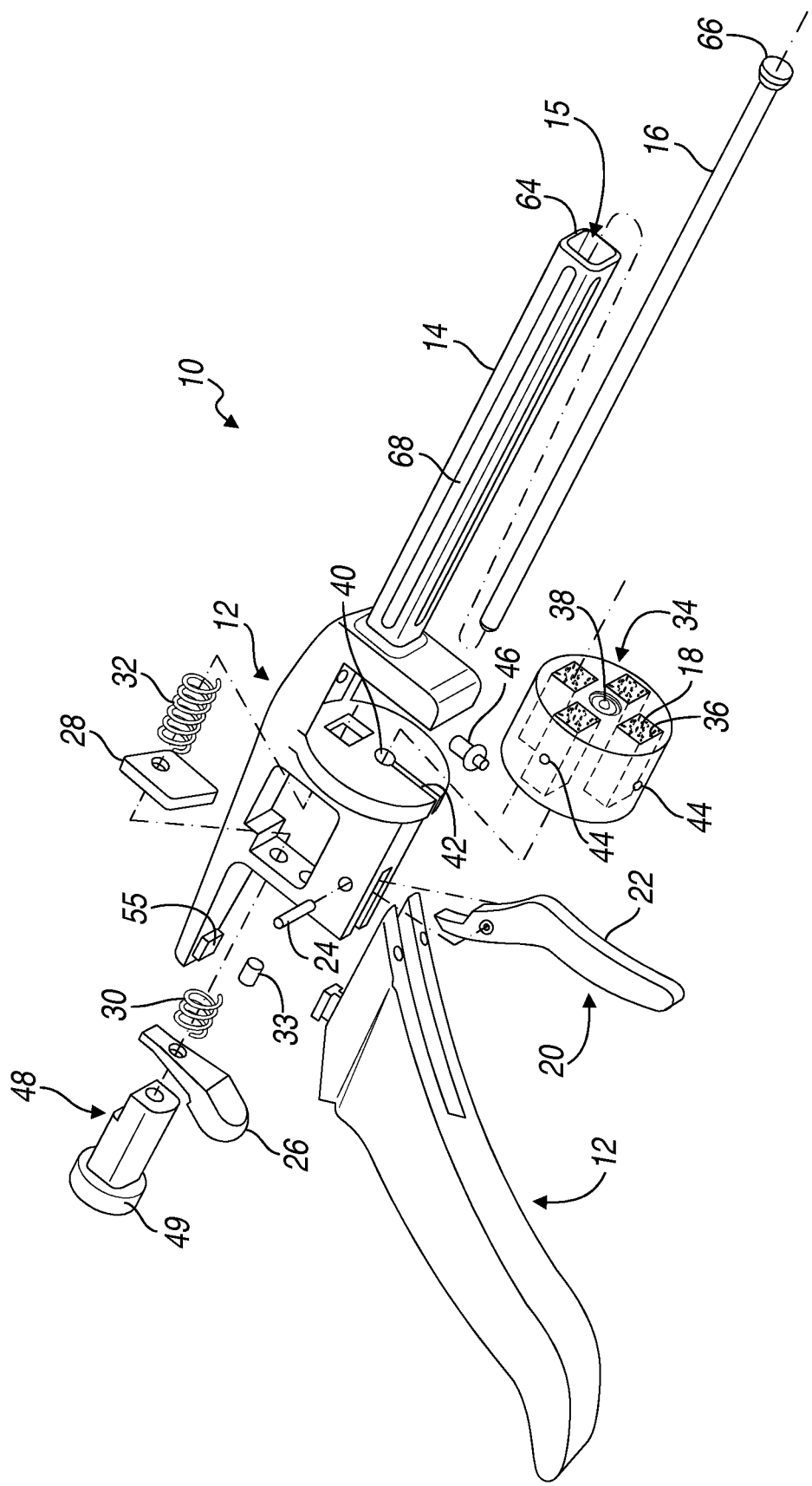
FIG. 2 is an exploded perspective view of the apparatus of FIG. 1.
Figure 3A:
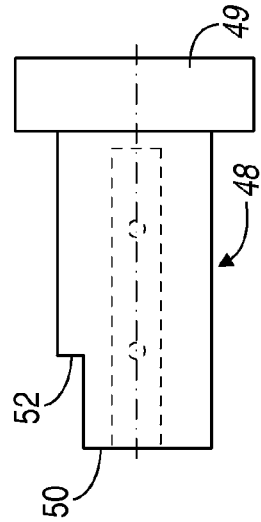
FIG. 3A is a side elevation view of the stop and selector member of the apparatus of FIG. 1.
Figure 3B:
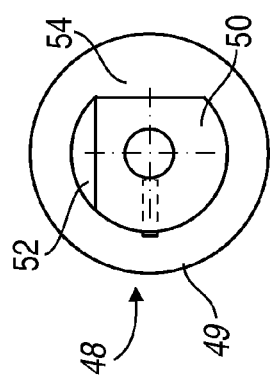
FIG. 3B is an end elevation view of the stop and selector member of FIG. 3.
Figure 4A:
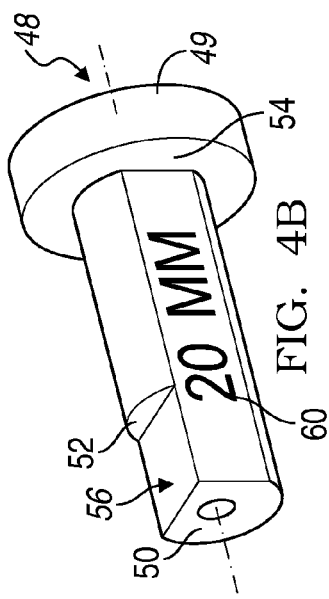
FIGS. 4A-4D are perspective views of the stop and selector member of FIG. 3.
Figure 4B:
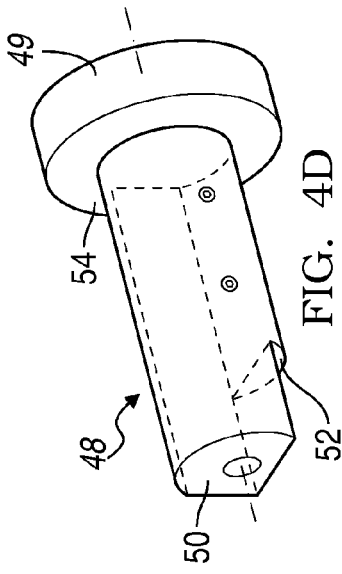
Figure 4C:
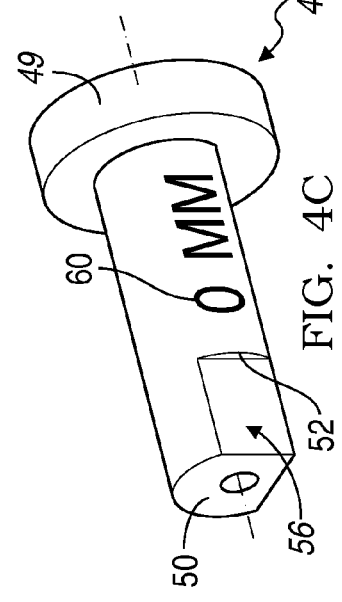
Figure 4D:
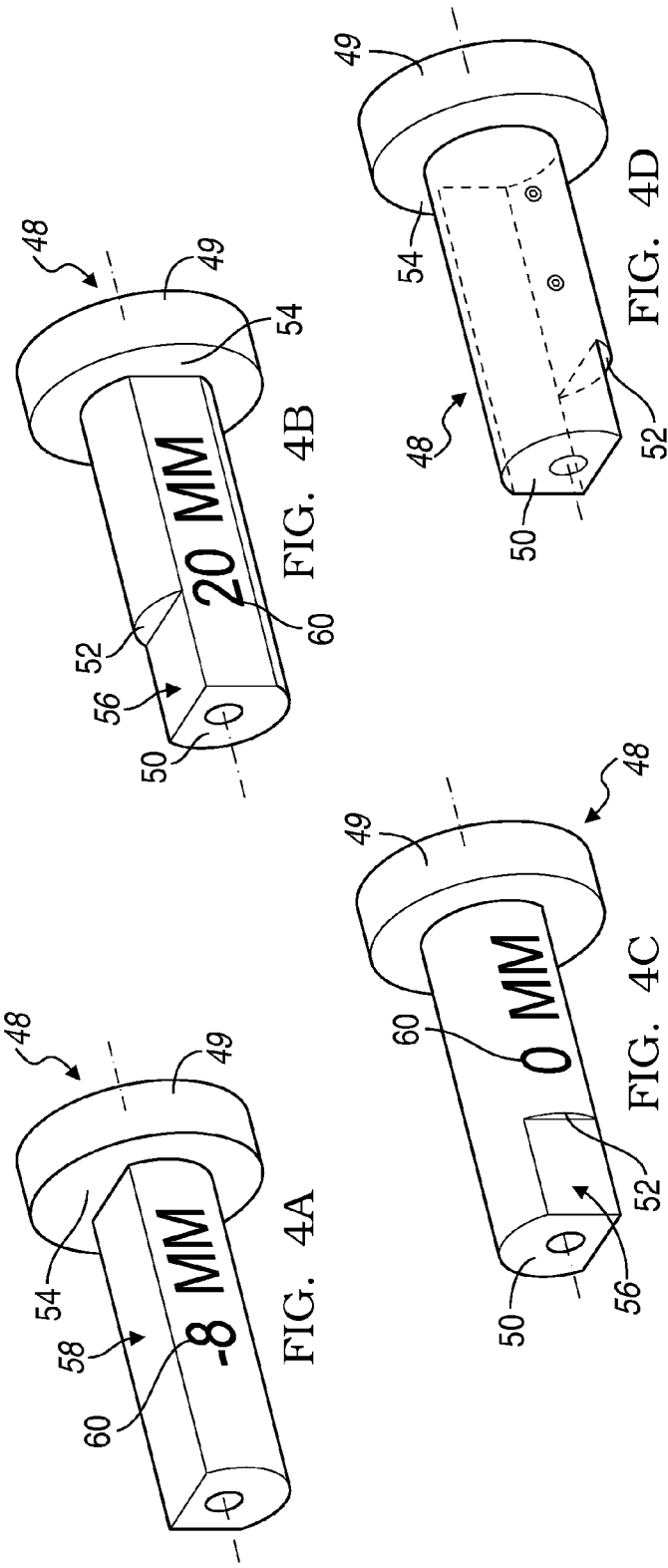

Referring to FIGS. 1 and 2, an exemplary bone graft delivery apparatus 10 generally includes a housing 12 comprising a barrel 14 defining a passageway 15, and a plunger 16 configured to advance the bone graft 18 through barrel 14 and its passageway 15.

A trigger mechanism 20 comprises trigger 22 coupled to housing 12 via pivot pin 24. Trigger mechanism 20 also comprises a plunger release plate 26 and a driving plate 28, each biased by a corresponding spring 30 and 32, respectively. Trigger mechanism 20 operates to drive plunger 16 down barrel 14 upon manual actuation of trigger 22. A plunger release plate 26 to be manually moved into an unlocked position against the biasing force of spring 30 until it engages stop 33, permitting plunger 16 to be manually withdrawn back along barrel 14.

A magazine 34 comprises a plurality of chambers 36, and each chamber 36 is configured to support a bone graft 18. In this case, four chambers 36 are provided in magazine 34. A spring loaded ball member 38 is centrally positioned to extend from each opposing side of magazine 34. Spring loaded ball members 38 cooperate with a detent 40 at the end of recess 42 of housing 12 to releasably couple magazine 34 to housing 12. A detent 44 on the outer circumferential surface of magazine 34 is associated with each chamber 36 to cooperate with a protrusion 46 of housing 12 when the chamber 36 is in an angular position such that it is aligned with plunger 16 and barrel 14.

An elongate member 48 is provided at the proximal end of plunger 16. Elongate member 48 includes an enlarged knurled knob 49 to facilitate a surgeon rotating the elongate member 48 into one of a plurality of selected angular positions. Thus, in this case, selector knob 49 is an integral part of elongate member 48. Each selected angular position corresponds to one of a plurality of stops 50, 52, 54 of elongate member 48. When selected, each stop 50, 52, 54 of the elongate member 48 engages a cooperating stop 55 of housing 12 to prevent plunger 16 from moving beyond a predetermined position corresponding to the selected stop 50, 52, or 54.

With additional reference to FIGS. 3A-4D, an end surface 50 at a first angular position of elongate member 48 operates as a first stop. An end surface 52 of a channel 56 extending partially along the length of elongate member 48 at a second angular position operates as a second stop. An end surface 54 of a channel 58 extending along substantially an entire length of elongate member 48 at a third angular position operates as a third stop. As illustrated, channels 56 and 58 do not have sides, but such can be provided.

To operate the bone graft dispensing device 10, plunger 16 is withdrawn from barrel 14 so that magazine 34 can be coupled to housing 12. Spring loaded ball members 38 are aligned with and manipulated down recess 42 until spring loaded ball members 38 engage with cooperating detents 40; thereby removably coupling magazine 34 to housing 12. If necessary, magazine 34 is rotated until housing protrusion 46 engages one of positioning detents 44 that corresponds to a chamber 36 supporting a bone graft 18.

A surgeon can rotate the elongate member into the first position. Elongate member 48 can include indicia 60 to identify the correct angular positioning to the surgeon. In this case, indicia 60 is positioned on the outer periphery of elongate member 48 adjacent each stop 50, 52, 54. Thus, indicia 60 is directly in the surgeon's line of sight as bone graft dispensing device 10 is held in his or her hand. Alternatively, indicia 60 can be provided on the outer end surface of elongate member 48. In either case, indicia 60 can be aligned with a known position relative to housing 12, which can include corresponding indicia (e.g., arrow) 62.

A surgeon can position the distal end 64 of the barrel 14 adjacent a spinal disc space (not shown). Prior to or after such positioning, the surgeon can actuate trigger mechanism 20 which advances the distal end 66 of plunger 16 along barrel 14; thereby advancing bone graft 18 along barrel 14. Barrel 14 includes slots 68 allowing the surgeon to visually verify the position of bone graft 18 along substantially the entire length of barrel 14.

With repeated actuation of trigger mechanism 20, the surgeon can advance plunger 16 and bone graft 18 along barrel 14 until the selected stop 50, 52, or 54 engages corresponding stop 55 of housing 12. As illustrated in FIGS. 5A and 5B, the first stop 50 can stop plunger 16 in a first predetermined position corresponding to a ready position, with bone graft 18 retained by barrel 14 adjacent distal end 64 of barrel 14. Thus, bone graft 18 can be fully inside passageway 15 of barrel 14, but close to its distal end 64, or bone graft 18 can extend partly beyond distal end 64 of barrel 14 as seen in FIG. 5B. In either case, barrel 14 and its passageway 15 can be configured to retain bone graft 18 when bone graft 18 is in the ready position.

The size of bone graft 18 can affect the specific distance that distal end 66 of plunger 16 is short of distal end 64 of barrel 14 (or passageway 15) in the ready position. In some cases, distal end 66 of plunger 16 can be less than about 30 mm short of distal end 64 of barrel 14 when plunger 16 is in the predetermined ready position with cooperating stops 50 and 55 engaged against each other. In some cases, distal end 66 of plunger 16 can be from about 5 mm to about 30 mm short of distal end 64 of barrel 14 when plunger 16 is in the ready position. In some cases, distal end 66 of plunger 16 can be about 8 mm short of distal end 64 of barrel 14 when plunger 16 is in the ready position.

When the surgeon is ready to dispense bone graft from the delivery apparatus 10, the surgeon can rotate elongate member 48 into the second position. As illustrated in FIGS. 6A and 6B, actuation of trigger mechanism 20 advances plunger 16 along barrel 14 until second stop 52 engages cooperating stop 55 of housing 12. Second stop 52 can stop plunger 16 in a second predetermined position corresponding to a dispensing position where bone graft 18 is no longer retained by barrel 14 and is released.

As noted above, different situations may call for different dimensions, but in some cases, distal end 66 of plunger 16 can be from about 2 mm short of distal end 64 of barrel 14 to about 2 mm beyond distal end 64 of barrel 14 when plunger 16 is in the dispensing position. In some cases, distal end 66 of plunger 16 can be substantially aligned with distal end 64 of barrel 14 when plunger 16 is in the dispensing position.

When the surgeon desires to reposition a dispensed bone graft 18, the surgeon can rotate elongate member 48 into the third position. As illustrated in FIGS. 7A and 7B, actuation of trigger mechanism 20 advances plunger 16 until third stop 54 engages cooperating stop 55 of housing 12. Third stop 54 can stop plunger 16 in a second predetermined position corresponding to a manipulating position where distal end 66 of plunger extends a predetermined distance beyond distal end 64 of barrel 14. Surgeon can then reposition dispensed bone graft 18 within the spinal disc space. Thus, distal end 66 of plunger 16 is configured to accomplish this task.

As noted above, different situations may call for different dimensions, but in some cases, distal end 66 of plunger 16 can extend less than about 30 mm beyond distal end 64 of barrel 14 when plunger 16 is in the predetermined manipulating position. In some cases, distal end 66 of plunger 16 can extend from about 10 mm to about 25 mm beyond distal end 64 of barrel 14 when plunger 16 is in the predetermined manipulating position. In some cases, distal end 66 of plunger 16 can extend about 20 mm beyond distal end 64 of barrel 14 when plunger 16 is in the predetermined manipulating position.

Surgeon can press plunger release plate 26 against stop 33 causing plunger release plate 26 to rotate and allowing the surgeon to withdraw plunger 16 back to its starting position. The surgeon can rotate magazine 34 to the next chamber 36 holding a bone graft 18. The surgeon can also rotate selector knob 49 into the first stop position and repeat the process for multiple bone grafts 18, without having to completely reposition the bone graft delivery apparatus 10 within, or to completely remove and reinsert the bone graft delivery apparatus 10 into a body cavity opening.

Methods for providing a bone graft delivery apparatus 10 should also be apparent from the above. For example, methods can include configuring a longitudinal passageway 15 and a plunger 16 movable along the passageway to push a bone graft 18 along passageway 15.

A stop mechanism 48, 55 is provided and configured to selectively prevent plunger 16 from moving past a predetermined ready position with bone graft 18 being held by passageway 15 adjacent a distal end 64 of passageway 15. Stop mechanism 48, 55 can also be configured to selectively prevent plunger 16 from moving past a predetermined dispensing position with a distal end 66 of the plunger 16 substantially aligned with the distal end 64 of the passageway 15. Stop mechanism 48, 55 can additionally be configured to selectively permit plunger 16 to move past the predetermined dispensing position to extend distal end 66 of plunger 16 beyond distal end 64 of the passageway 15.

Stop mechanism 48, 55 can further be configured to selectively prevent plunger 16 from moving past a predetermined manipulating position with distal end 66 of plunger 16 extending a predetermined distance beyond distal end 64 of passageway 15. Distal end of plunger 16 can be configured to reposition bone graft 18 in a spinal disc space after bone graft 18 has been dispensed from passageway 15.

A trigger mechanism 20 can be provided and configured to advance plunger 16 along passageway 15. A magazine 34 can be provided and configured to support bone grafts 18 in chambers 36 configured to be selectively aligned with passageway 15 and plunger 16. Magazine 34 can additionally be configured to be retained in the various alignment positions (e.g., via detent 44 and cooperating protrusion 46 of housing 12).

The terminology used herein is for the purpose of describing a particular example embodiment only and is not intended to be limiting. For example, the terms first, second, third are used herein to differentiate the various stops from each other, such terms do not imply a sequence or order unless clearly indicated by the context. Thus, a first stop could be termed a second stop elsewhere in this disclosure and claims, and without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A bone graft delivery apparatus comprising:
   a housing comprising a barrel and a handle;
   a magazine coupled to the housing and having a plurality of chambers, each of the chambers being configured to receive a bone graft;
   a plunger supported by the housing that is extendable through a selected one of the chambers and along a passage disposed in the barrel,
   an elongate member coupled to the proximal end of the plunger, the elongate member defining a plurality of stops, wherein each stop of the plurality of stops is positioned uniquely with respect to the other stops both radially about an outer surface of the elongate member and along a length of the elongate member, wherein each stop of the plurality of stops is engageable with a housing stop of the housing;
   a selector knob operably coupled to a proximal end of the elongate member such that rotation of the selector knob rotates the elongate member about a longitudinal axis extending along the length of the elongate member, the selector knob being rotatable to a plurality of positions, each of the plurality of positions corresponding to a radial position of one stop of the plurality of stops;
   a trigger mechanism supported by the housing and operably coupled to the plunger, wherein, upon actuation, the trigger mechanism advances the plunger along the passage of the barrel until a selected stop of the plurality of stops engages the housing stop;
   wherein a first stop of the plurality of stops prevents the plunger from advancing past a first predetermined plunger position, and wherein a second stop of the plurality of stops prevents the plunger from advancing past a second predetermined plunger position.

2. The bone graft delivery apparatus of claim 1, wherein the magazine is removably coupled to the housing.

3. The bone graft delivery apparatus of claim 1, wherein the first stop causes the plunger to advance the bone graft into a distal portion of the barrel.

4. The bone graft delivery apparatus of claim 1, wherein the barrel comprises a slot disposed therein that extends substantially the entire length of the barrel, thereby allowing a position of the bone graft within the passage to be seen.

5. The bone graft delivery apparatus of claim 1, wherein the second stop causes the plunger to expel the bone graft from the distal end of the barrel.

6. The bone graft delivery apparatus of claim 1, wherein the first predetermined plunger position and the second predetermined plunger position are located within the passage, wherein a third stop of the plurality of stops causes the plunger to advance to a third predetermined plunger position where the distal end of the plunger extends beyond the distal end of the barrel.

7. The bone graft delivery apparatus of claim 6, wherein the the distal end of the plunger is engageable with the bone graft to reposition the bone graft in a spinal disc space after the bone graft has been expelled from the barrel.

8. A bone graft delivery apparatus comprising:
a housing comprising a barrel and a handle;
a magazine rotatably coupled to the housing and having a plurality of chambers, each of the chambers being configured to receive a bone graft;
a plunger supported by the housing and that is extendable through a selected one of the chambers and along a passage disposed in the barrel,
an elongate member coupled to the proximal end of the plunger, the elongate member defining a plurality of stops, wherein each stop of the plurality of stops is positioned uniquely with respect to the other stops both radially about an outer surface of the elongate member and along a length of the elongate member, wherein each stop of the plurality of stops is engageable with a housing stop of the housing;
a selector knob operably coupled to a proximal end of the elongate member such that rotation of the selector knob rotates the elongate member about a longitudinal axis extending along the length of the elongate member, the selector knob being rotatable to a plurality of positions, each of the plurality of positions corresponding to a radial position of one stop of the plurality of stops;
a trigger mechanism supported by the housing and operably coupled to the plunger, wherein, upon actuation, the trigger mechanism advances the plunger along the passage of the barrel until a selected stop of the plurality of stops engages the housing stop;
wherein a first stop of the plurality of stops prevents a distal end of the plunger from moving beyond a first predetermined plunger position that lies within a distal portion of the passage, and wherein a second stop of the plurality of stops prevents the distal end of the plunger from moving beyond a second predetermined plunger position that is substantially aligned with the distal end of the barrel.

9. The bone graft delivery apparatus of claim 8, wherein a third stop of the plurality of stops prevents the distal end of the plunger from moving beyond a third predetermined plunger position that extends past the distal end of the barrel.

10. The bone graft delivery apparatus of claim 8, wherein the first stop causes the plunger to advance the bone graft into a distal portion of the barrel.

11. The bone graft delivery apparatus of claim 8, wherein the second stop causes the plunger to expel the bone graft from the distal end of the barrel.

12. The bone graft delivery apparatus of claim 8, wherein the magazine is removably coupled to the housing.

13. The bone graft delivery apparatus of claim 8, wherein the barrel comprises a slot disposed therein that extends substantially the entire length of the barrel, thereby allowing a position of the bone graft within the passage to be seen.

14. The bone graft delivery apparatus of claim 9, wherein the distal end of the plunger is engageable with the bone graft to reposition the bone graft in a spinal disc space after the bone graft has been expelled from the barrel.

* * * * *

UNITED STATES PATENT AND TRADEMARK OFFICE
CERTIFICATE OF CORRECTION

PATENT NO. : 9,545,282 B2
APPLICATION NO. : 13/791925
DATED : January 17, 2017
INVENTOR(S) : Mathur et al.

It is certified that error appears in the above-identified patent and that said Letters Patent is hereby corrected as shown below:

In the Claims

In Column 7, Line 2, in Claim 7, delete "the the" and insert --the-- therefor

Signed and Sealed this
Twelfth Day of June, 2018

Andrei Iancu
*Director of the United States Patent and Trademark Office*